(12) United States Patent
Watanabe et al.

(10) Patent No.: US 9,518,036 B2
(45) Date of Patent: Dec. 13, 2016

(54) METHOD FOR PRODUCING ETHYLENE OXIDE

(71) Applicant: NIPPON SHOKUBAI CO., LTD., Osaka (JP)

(72) Inventors: Akimasa Watanabe, Kanagawa (JP); Takahiro Takinami, Kanagawa (JP); Noriji Morikawa, Kanagawa (JP)

(73) Assignee: NIPPON SHOKUBAI CO., LTD., Chuo-Ku, Osaka-Shi, Osaka (JP)

( * ) Notice: Subject to any disclaimer, the term of this patent is extended or adjusted under 35 U.S.C. 154(b) by 0 days.

(21) Appl. No.: 14/781,245

(22) PCT Filed: Mar. 28, 2014

(86) PCT No.: PCT/JP2014/059346
§ 371 (c)(1),
(2) Date: Sep. 29, 2015

(87) PCT Pub. No.: WO2014/157699
PCT Pub. Date: Oct. 2, 2014

(65) Prior Publication Data
US 2016/0052900 A1   Feb. 25, 2016

(30) Foreign Application Priority Data
Mar. 29, 2013   (JP) .................. 2013-075050

(51) Int. Cl.
*C07D 301/10* (2006.01)
*C07D 301/32* (2006.01)
*B01D 53/14* (2006.01)
*B01D 53/62* (2006.01)
*B01D 53/78* (2006.01)

(52) U.S. Cl.
CPC ......... *C07D 301/10* (2013.01); *B01D 53/1487* (2013.01); *B01D 53/62* (2013.01); *B01D 53/78* (2013.01); *C07D 301/32* (2013.01); *B01D 2251/304* (2013.01); *B01D 2251/306* (2013.01); *B01D 2251/604* (2013.01); *B01D 2252/103* (2013.01); *B01D 2256/24* (2013.01); *B01D 2257/504* (2013.01); *Y02C 10/04* (2013.01); *Y02C 10/06* (2013.01); *Y02P 20/121* (2015.11); *Y02P 20/124* (2015.11); *Y02P 20/152* (2015.11); *Y02P 20/51* (2015.11)

(58) Field of Classification Search
CPC .............................. C07D 301/10; C07D 301/32
See application file for complete search history.

(56) References Cited

U.S. PATENT DOCUMENTS 4,778,567 A   10/1988   Kakimoto et al.
6,397,599 B1 *   6/2002   Theis .................... C07C 29/106
                                                            60/649

(Continued)

FOREIGN PATENT DOCUMENTS

| JP | 60-131817 | 7/1985 |
| JP | 63-017873 | 1/1988 |
| JP | 63017873 A | 1/1988 |
| JP | 63-030476 | 2/1988 |
| JP | 63030476 A | 2/1988 |
| JP | 63-170206 | 7/1988 |
| JP | 63170206 A | 7/1988 |
| JP | 2012-214399 | 11/2012 |

OTHER PUBLICATIONS

International Preliminary Report on Patentability dated Oct. 8, 2015 issued in International Patent Application No. PCT/JP2014/059346 which corresponds to the present application.
Tadasue, Itsuo. "Ethylene Oxide, Ethylene Glycol." Petrotech, vol. 20(3): 248-253 (1997).

*Primary Examiner* — Golam M M Shameem
(74) *Attorney, Agent, or Firm* — Porzio, Bromberg & Newman, P.C.

(57) ABSTRACT

[Problem] To provide a novel technology by which energy efficiency can be further improved in a process for producing ethylene oxide.
[Solution] A method for producing ethylene oxide including: an ethylene oxidation reaction step in which ethylene is subjected to catalytic vapor-phase oxidation using a molecular oxygen-containing gas in the presence of a silver catalyst; supplying an ethylene oxide-containing reaction product gas produced in the ethylene oxidation reaction step to an ethylene oxide absorption column; bringing the reaction product gas into contact with an absorption liquid supplied to the ethylene oxide absorption column; supplying an ethylene oxide-containing column bottom liquid of the ethylene oxide absorption column to an ethylene oxide purification system; purifying ethylene oxide in the ethylene oxide purification system; supplying at least a part of a carbon dioxide gas-containing gas discharged from a column top part of the ethylene oxide absorption column to a carbon dioxide gas absorption column; extracting a carbon dioxide gas-rich absorption liquid obtained by contact of the carbon dioxide gas-containing gas with an absorption liquid as a column bottom liquid of the carbon dioxide gas absorption column; supplying the carbon dioxide gas-rich absorption liquid to an upper part of the carbon dioxide gas stripper column; stripping the carbon dioxide gas from the carbon dioxide gas-rich absorption liquid; and discharging the carbon dioxide gas from a column top part of the carbon dioxide gas stripper column as an exhaust gas, the ethylene oxide purification system including an ethylene oxide purification column provided with a reboiler in a lower part thereof, and a heating medium for heating the reboiler being heated by heat exchange with the exhaust gas.

1 Claim, 4 Drawing Sheets

(56) References Cited

U.S. PATENT DOCUMENTS

| | | | | |
|---|---|---|---|---|
| 8,580,982 B2* | 11/2013 | Seeber | ............... | C07D 301/10 |
| | | | | 549/536 |
| 8,716,175 B2* | 5/2014 | Nakashiro | ............. | B01J 23/688 |
| | | | | 502/241 |
| 9,090,577 B2* | 7/2015 | Hashimoto | ........... | B01J 23/002 |

* cited by examiner

METHOD FOR PRODUCING ETHYLENE OXIDE

TECHNICAL FIELD

The present invention relates to a method for producing ethylene oxide.

BACKGROUND ART

Nowadays, ethylene oxide is produced by catalytic gas phase oxidation of ethylene using a molecular oxygen-containing gas in the presence of a silver catalyst. An outline of a purifying method in a process for producing ethylene oxide is as follows (for example, refer to JP 62-103072 A).

First, ethylene and a molecular oxygen-containing gas are subjected to catalytic gas phase oxidation on a silver catalyst to obtain an ethylene oxide-containing reaction product gas (reaction step). Subsequently, the resulting reaction product gas is introduced into an ethylene oxide absorption column. The reaction product gas is brought into contact with an absorption liquid mainly containing water. Ethylene oxide is recovered as an aqueous solution (absorption step). Subsequently, the recovered ethylene oxide aqueous solution is fed to a purification system of ethylene oxide to obtain high-purity ethylene oxide through several stages. The ethylene oxide purification system usually includes a stripping step, a dehydration step, a light fraction separation step, a heavy fraction separation (purification) step, and the like.

Many steps in the process for producing ethylene oxide (for example, a heavy fraction separation (purification) step in a purification system) require thermal energy, and water vapor is mainly used as a supplying source thereof. Therefore, when a production amount of ethylene oxide is increased, an amount of water vapor as a thermal energy source is also increased. This increases running cost and reduces a profit.

In the related art, as a technology for recovering a thermal energy in a process for producing ethylene oxide, the following technology is proposed. That is, water vapor is generated using reaction heat generated in a reaction step to be used as a power source of a pump or the like, a driving source of a generator, or process steam of an ethylene oxide production plant and an ethylene glycol production plant (for example, refer to JP 2012-214399 A). As an example of recovering exhaust heat of an exhaust gas from a column top of a distillation column, a technology is known, in which exhaust heat of an exhaust gas from a column top of an ethylene oxide stripper column is recovered as a heat source of an ethylene oxide purification column (for example, refer to JP 63-30476 A).

By the way, in the related art, an exhaust gas containing unreacted ethylene discharged from a column top part of the ethylene oxide absorption column, a carbon dioxide gas (carbon dioxide; $CO_2$) and water as by-products, and an inert gas (nitrogen, argon, methane, ethane, or the like) is circulated into an ethylene oxidation step as it is. Alternatively, a part thereof is extracted and introduced into a carbon dioxide gas absorption column, and the carbon dioxide gas is selectively absorbed by an alkali absorption liquid. The absorption liquid is supplied to a carbon dioxide gas stripper column to strip and recover the carbon dioxide gas (for example, refer to JP 60-131817 A). Further, a carbon dioxide gas-containing gas containing a carbon dioxide gas stripped and recovered in a carbon dioxide gas stripper column is usually discharged from a column top part of the carbon dioxide gas stripper column to be purged into the atmosphere (for example, refer to "Ethylene oxide, Ethylene glycol" written by Itsuo Tadasue, PETROTECH, Vol. 20, No. 3 (1997)).

SUMMARY OF INVENTION

Technical Problem

As described above, in the related art, various technologies are proposed in order to save energy in a process for producing ethylene oxide. However, presently, it is hard to say that energy-saving of the process has been achieved sufficiently even if the above-described technologies are employed. Now, it is desired to further improve energy efficiency. Particularly, the improvement of the energy efficiency in the process for producing ethylene oxide is very small from a short-term viewpoint. However, in view of the present production amount of ethylene oxide of hundreds of thousands tons per year, an economic advantage thereof is immeasurable.

Therefore, an object of the present invention is to provide a novel technology by which energy efficiency can be further improved in a process for producing ethylene oxide.

Means for Solving Problem

The present inventors conducted intensive studies to further improve energy efficiency in a process for producing ethylene oxide. As a result, the inventors have found that the above-described problems can be solved by using exhaust heat of an exhaust gas from a column top of a carbon dioxide gas stripper column as a heat source of an ethylene oxide purification column in an ethylene oxide purification system, and have completed the present invention.

That is, an aspect of the present invention relates to a method for producing ethylene oxide. The production method includes: an ethylene oxidation reaction step in which ethylene is subjected to catalytic vapor-phase oxidation using a molecular oxygen-containing gas in the presence of a silver catalyst; supplying an ethylene oxide-containing reaction product gas produced in the ethylene oxidation reaction step to an ethylene oxide absorption column; bringing the reaction product gas into contact with an absorption liquid supplied to the ethylene oxide absorption column; supplying an ethylene oxide-containing column bottom liquid of the ethylene oxide absorption column to an ethylene oxide purification system; and purifying ethylene oxide in the ethylene oxide purification system. In addition, the production method includes: supplying at least a part of a carbon dioxide gas-containing gas discharged from a column top part of the ethylene oxide absorption column to a carbon dioxide gas absorption column; extracting a carbon dioxide gas-rich absorption liquid obtained by contact of the carbon dioxide gas-containing gas with an absorption liquid as a column bottom liquid of the carbon dioxide gas absorption column; supplying the carbon dioxide gas-rich absorption liquid to an upper part of the carbon dioxide gas stripper column; stripping the carbon dioxide gas from the carbon dioxide gas-rich absorption liquid; and discharging the carbon dioxide gas from a column top part of the carbon dioxide gas stripper column as an exhaust gas.

The method for producing ethylene oxide according to the present aspect is characterized in that the ethylene oxide purification system includes an ethylene oxide purification column provided with a reboiler in a lower part thereof, and that a heating medium for heating the reboiler of the ethylene oxide purification column is heated by heat exchange with the above-described exhaust gas from the column top part of the carbon dioxide gas stripper column.

Advantageous Effect of the Invention

According to the present invention, in a process for producing ethylene oxide, a heat source used to heat a heating medium (warm water or the like) of a reboiler of an ethylene oxide purification column in the related art, such as water vapor, is not necessary. As a result, such an industrially extremely advantageous effect that energy efficiency in the process for producing ethylene oxide is further improved is exhibited.

BRIEF DESCRIPTION OF DRAWINGS

FIG. 1 corresponds to the process employed in the Example described later.

FIG. 2 corresponds to a stripping step employed in the Example described later.

FIG. 4 corresponds to a process employed in the Comparative Example described later.

DESCRIPTION OF EMBODIMENTS

Hereinafter, specific embodiments for carrying out the present invention will be described in detail with reference to the drawings. However, the technical range of the present invention should be determined based on the description of claims, and is not limited only to the following embodiment.

<<Reaction System>>

Figure 1:
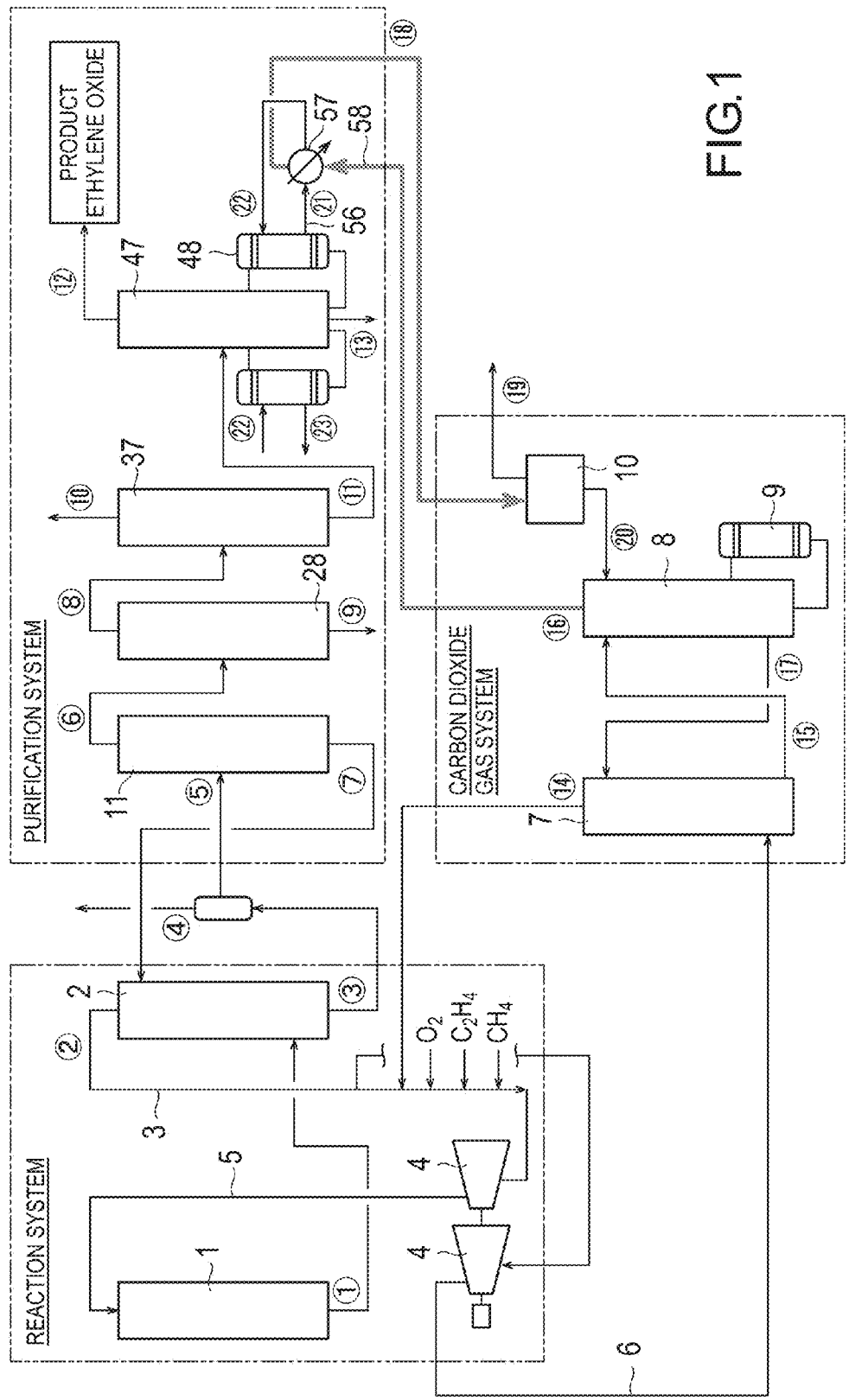
FIG. 1 is a block diagram illustrating a structure example of a production process for performing a method for producing ethylene oxide according to an embodiment of the present invention.

First, a system of producing ethylene oxide by an oxidation reaction of ethylene (hereinafter, also simply referred to as "reaction system") will be described with reference to FIG. 1. FIG. 1 is a block diagram illustrating a constructive example of a process for producing ethylene oxide, performing a method for recovering carbon dioxide according to an embodiment of the present invention. The process for producing ethylene oxide illustrated in FIG. 1 is roughly divided into three systems of a reaction system, a carbon dioxide gas system, and a purification system. FIG. 1 corresponds to the process employed in the Example described later.

"An ethylene oxide-containing reaction product gas" used in the present invention is only required to be produced by a step in which ethylene is subjected to catalytic gas phase oxidation using a molecular oxygen-containing gas in the presence of a silver catalyst (hereinafter, also referred to as "ethylene oxidation reaction step"). The technology itself of the catalytic gas phase oxidation reaction is popular, and conventionally known knowledge thereof can be appropriately referred to in order to carry out the present invention. Specific embodiments such as a composition of the reaction product gas are not particularly limited. As an example, the reaction product gas usually contains, in addition to ethylene oxide in an amount of 0.5 to 5% by volume, unreacted oxygen, unreacted ethylene, generated water, a gas such as carbon dioxide, nitrogen, argon, methane, or ethane, an aldehyde such as formaldehyde or acetaldehyde, and a small amount of an organic acid such as acetic acid.

When FIG. 1 is referred to, first, a raw material gas containing ethylene or molecular oxygen is boosted by a boosting blower 4, and then is heated by a heat exchanger (not illustrated) to be supplied to an ethylene oxidation reactor 1. The ethylene oxidation reactor 1 is usually a multi-tubular reactor provided with many reaction tubes filled with a silver catalyst. The reaction product gas produced in the ethylene oxidation reaction step is cooled by passing through a heat exchanger (not illustrated). Thereafter, the reaction product gas is supplied to an ethylene oxide absorption column (hereinafter, also simply referred to as "absorption column") 2. Specifically, the reaction product gas is supplied from a column bottom part of the absorption column 2. Meanwhile, an absorption liquid mainly containing water is supplied from a column top part of the absorption column 2. Counter flow contact between a gas and a liquid is thereby conducted in the absorption column 2. Ethylene oxide (usually, 99% by weight or more) included in the reaction product gas is absorbed in the absorption liquid. In addition to ethylene oxide, ethylene, oxygen, carbon dioxide, an inert gas (nitrogen, argon, methane, ethane, or the like), a low boiling point impurity such as formaldehyde, and a high boiling point impurity such as acetaldehyde or acetic acid, which are produced in the ethylene oxidation reaction step, are absorbed at the same time in substantial amounts thereof. The temperature of the reaction product gas supplied to the absorption column 2 is preferably about 20 to 80° C. A composition of the absorption liquid is not particularly limited. In addition to a liquid mainly containing water, such propylene carbonate as disclosed in JP 8-127573 A may be used as an absorption liquid. An additive can be added to the absorption liquid as necessary. Examples of the additive which can be added to the absorption liquid include a defoaming agent and a pH adjusting agent. As the defoaming agent, any defoaming agent which is insert to ethylene oxide, ethylene glycol as a by-product, or the like, and has a defoaming effect of the absorption liquid can be used. However, a typical example thereof is a water-soluble silicone emulsion because the water-soluble silicone emulsion is effective due to excellent dispersibility in the absorption liquid, excellent dilution stability, and excellent thermal stability. Examples of the pH adjusting agent include a compound which can be dissolved in the absorption liquid, such as a hydroxide or a carbonate of an alkali metal such as potassium or sodium. Preferable examples thereof include potassium hydroxide and sodium hydroxide. The pH of the absorption liquid is preferably 5 to 12, more preferably 6 to 11.

As the absorption column 2, a plate column type or packed column type absorption column can be usually used. As an operation condition of the absorption column 2, a concentration of ethylene oxide in the reaction product gas is 0.5 to 5% by volume, preferably 1.0 to 4% by volume, and an operation pressure of the absorption column 2 is 0.2 to 4.0 MPa gauge, preferably 1.0 to 3.0 MPa gauge. An absorption operation is more advantageous as the pressure is higher. However, a possible value thereof can be determined according to an operation pressure of the oxidation reactor. A molar ratio of flow rate (L/V) of the absorption liquid with respect to the reaction product gas is usually 0.30 to 2.00. A space linear velocity (GHSV[NTP]) of the reaction product gas under the standard state is usually 400 to 6000 $h^{-1}$.

A gas not absorbed in the absorption column 2, containing ethylene, oxygen, carbon dioxide, an inert gas (nitrogen, argon, methane, or ethane), aldehyde, an acid substance, or the like, is discharged from the column top part of the absorption column 2 through a conduit 3. The exhaust gas is boosted by the boosting blower 4, and then is circulated into the ethylene oxidation reactor 1 through a conduit 5. Details of the ethylene oxidation reaction step are as described above. Here, the ethylene oxidation reaction step is usually carried out in an oxidation reactor provided with many reaction tubes filled with a silver catalyst under pressure (pressure of about 1.0 to 3.0 MPa gauge). Therefore, it is necessary to boost the exhaust gas from the column top part of the absorption column 2 using a boosting unit such as the boosting blower 4 before the exhaust gas is circulated into the ethylene oxidation reaction step.

<<Carbon Dioxide Gas System>>

In a preferable embodiment, as illustrated in FIG. 1, at least a part of the gas discharged from the column top part of the absorption column 2 (carbon dioxide gas-containing gas) is boosted by a boosting unit such as the boosting blower 4 to be supplied to a carbon dioxide gas absorption column 7 through a conduit 6. Hereinafter, a carbon dioxide gas recovery system (hereinafter, also simply referred to as "carbon dioxide gas system") starting from introduction of a gas into the carbon dioxide gas absorption column 7 will be described with reference to FIG. 1.

As described above, when the gas discharged from the column top part of the absorption column 2 is boosted and introduced into the carbon dioxide gas absorption column 7 (via the conduit 6), the gas pressure at that time is adjusted to about 0.5 to 4.0 MPa gauge, and the gas temperature is adjusted to about 80 to 120° C. A carbon dioxide gas stripper column 8 is disposed in a post-stage of the carbon dioxide gas absorption column 7. An alkali absorption liquid is supplied from a column bottom part of the carbon dioxide gas stripper column 8 to an upper part of the carbon dioxide gas absorption column 7. A carbon dioxide gas and a small amount of inert gas (for example, ethylene, methane, ethane, oxygen, nitrogen, argon), contained in the gas introduced into the carbon dioxide gas absorption column 7, are absorbed by counter flow contact with the alkali absorption liquid. An unabsorbed gas discharged from the column top part of the carbon dioxide gas absorption column 7 is circulated into the conduit 3, is mixed with oxygen, ethylene, methane, or the like newly replenished, and then is circulated into the ethylene oxidation reactor 1.

The carbon dioxide gas-rich absorption liquid which has absorbed the carbon dioxide gas in the carbon dioxide gas absorption column 7 is extracted from the column bottom part of the carbon dioxide gas absorption column. Thereafter, the pressure thereof is adjusted to 0.01 to 0.5 MPa gauge, and the temperature thereof is adjusted to about 80 to 120° C. The carbon dioxide gas-rich absorption liquid is supplied to an upper part of the carbon dioxide gas stripper column 8 provided with a reboiler 9 at the column bottom part thereof. The absorption liquid causes pressure flash due to a pressure difference between the carbon dioxide gas absorption column 7 and the carbon dioxide gas stripper column 8 in a liquid feeding part in the upper part of the carbon dioxide gas stripper column 8. Because of the pressure flash, 10 to 80% by volume of carbon dioxide gas and most inert gases in the absorption liquid are separated from the absorption liquid, and discharged from the column top part of the carbon dioxide gas stripper column 8 as an exhaust gas. One of the characteristics of the present invention is use of exhaust heat of the exhaust gas as a heat source of an ethylene oxide purification column in a purification system. Details thereof will be described later. Here, an operation pressure of the carbon dioxide gas stripper column 8 is preferably lower from the viewpoint of reducing an input amount of steam into the reboiler 9 of the carbon dioxide gas stripper column 8. Specifically, the operation pressure of the carbon dioxide gas stripper column 8 is preferably 0 to 0.1 MPa gauge, and more preferably 0.01 to 0.015 MPa gauge.

In the meantime, the remaining carbon dioxide gas absorption liquid after a part of the carbon dioxide gas is separated because of the above-described pressure flash enters a gas-liquid contact part 10 provided below the liquid feeding part. The carbon dioxide gas absorption liquid is subjected to counter flow contact with a gas mainly containing steam produced in the reboiler 9 and a carbon dioxide gas produced in the gas-liquid contact part 10 or in parts below the gas-liquid contact part 10. A part of the carbon dioxide gas in the absorption liquid and most of the other inert gases are separated from the absorption liquid. By a series of the processes in the carbon dioxide gas system, a high-purity carbon dioxide gas is obtained from a part ranging from the top to the lower part of the gas-liquid contact part 10, preferably from the inside of the carbon dioxide gas stripper column 8 below the gas-liquid contact part 10 corresponding to one or more number of theoretical stages, necessary for gas-liquid contact. That is, in the gas-liquid contact part 10, the inert gas in the carbon dioxide gas absorption liquid is subjected to counter flow gas-liquid contact by water vapor and a carbon dioxide gas containing an extremely small amount of inert gas which comes up from the lower part, and is stripped. This makes the concentration of the inert gas extremely low. Therefore, if the gas after being stripped is extracted, a high-purity carbon dioxide gas is obtained.

<<Purification System>>

Figure 2:
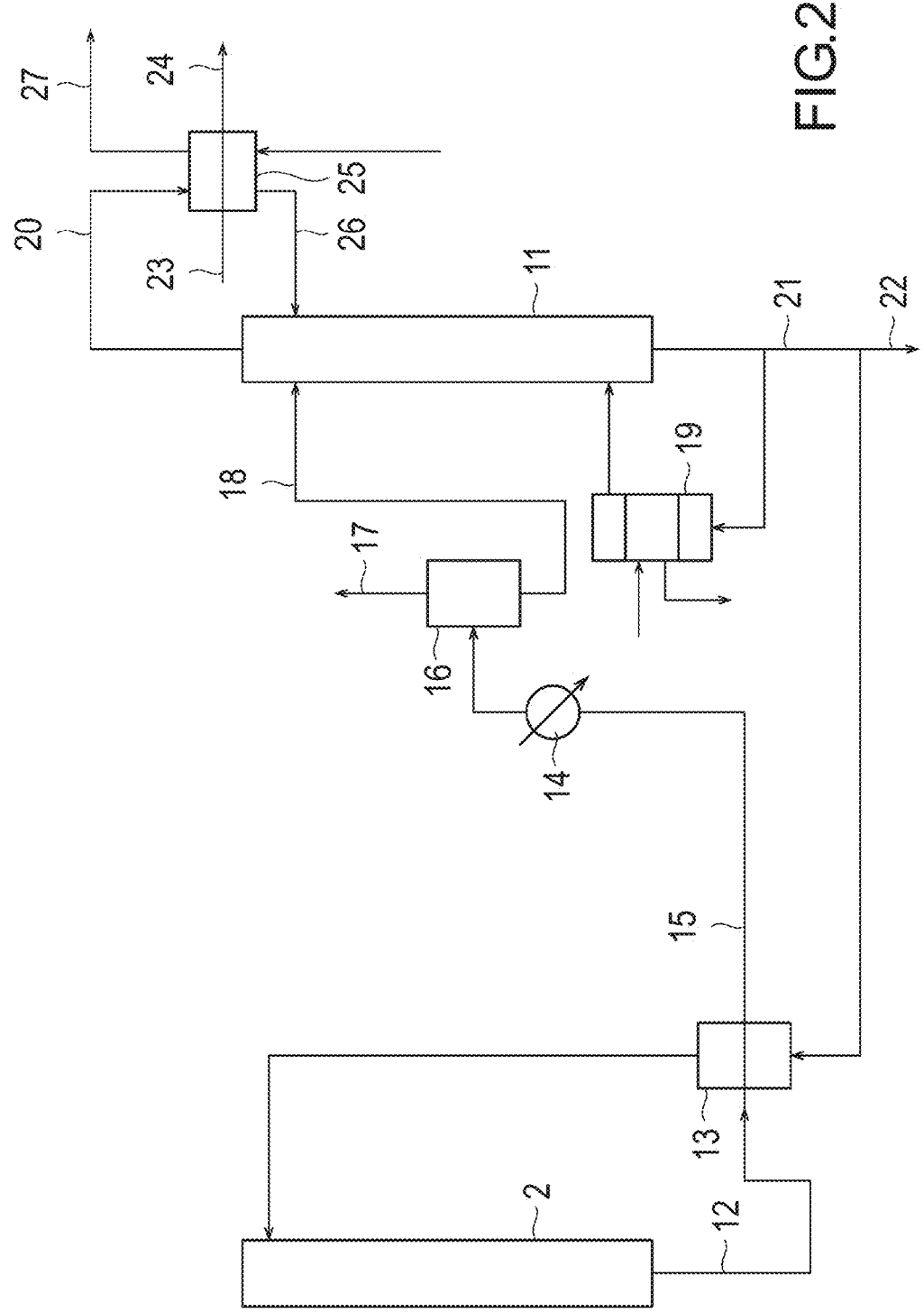
FIG. 2 is a block diagram illustrating a structure example of a process for performing a method for producing ethylene oxide according to an embodiment of the present invention.

The absorption liquid which has absorbed ethylene oxide in the absorption column 2 is fed to an ethylene oxide purification system (hereinafter, also simply referred to as "purification system") as a column bottom liquid of the absorption column 2. Specific embodiments of the purification system are not particularly limited. Conventionally known knowledge thereof can be appropriately referred to. The purification system usually includes a stripping step, a dehydration step, a light fraction separation step, a heavy fraction separation (purification) step, and the like. Hereinafter, a purification system including some of these steps will be described with reference to FIGS. 2 and 3. FIG. 2 is a block diagram illustrating a constructive example of a process for performing the process for producing ethylene oxide according to the embodiment of the present invention.

The column bottom liquid (absorption liquid) of the absorption column 2 is usually heated to a temperature suitable for stripping in an ethylene oxide stripper column (hereinafter, also simply referred to as "stripper column") 11 in advance before being supplied to the stripper column 11. Specifically, as illustrated in FIG. 2, the column bottom liquid (absorption liquid) of the absorption column 2 is supplied to a heat exchanger 13 through a conduit 12. In the heat exchanger 13, heat exchange with the column bottom liquid of the stripper column 11 is performed. Furthermore, if necessary, the column bottom liquid (absorption liquid) of the absorption column 2 is heated by a heater 14 to a temperature of about 70 to 110° C. In the present embodiment, the column bottom liquid (absorption liquid) of the absorption column 2, heated by heat exchange with the column bottom liquid of the stripper column 11, is supplied to a gas-liquid separation tank 16 through a conduit 15. In the gas-liquid separation tank 16, a light fraction gas of an inert gas partially including ethylene oxide and water is separated, and discharged through a conduit 17. On the other hand, the absorption liquid as a remaining part after the light fraction gas is flashed is supplied to an upper part of the stripper column 11 through a conduit 18. In a portion where ethylene oxide and water exist together at a particularly high temperature as in the conduit 18, staying time of the absorption liquid can be short by making a disposition distance thereof as short as possible. As a result, production of ethylene glycol as a by-product can be prevented.

Subsequently, for example, as illustrate in FIG. 2, a heating medium such as water vapor is supplied to a reboiler 19, and the stripper column 11 is heated using the heating medium heated in the reboiler 19. Alternatively, the stripper column 11 is heated by directly supplying water vapor to the column bottom part of the stripper column 11. By heating the stripper column 11 in such a manner, ethylene oxide contained in the absorption liquid supplied from the upper part of the stripper column 11 (usually 99% by weight or more thereof) is stripped and discharged from the column top part of the stripper column 11 through a conduit 20. As for operation conditions of the stripper column 11, the column top pressure is usually 0.01 to 0.20 MPa gauge, and preferably 0.03 to 0.06 MPa gauge. The smaller the column top pressure is, the lower the temperature in the column is. As a result, production of ethylene glycol as a by-product from ethylene oxide in the column tends to be suppressed. However, ethylene oxide is relatively easily ignitable. Therefore, from a viewpoint of preventing leakage of oxygen into the system, usually, the operation is not performed at atmospheric pressure or lower, and is performed at a pressure a little higher than atmospheric pressure. As for temperature conditions of the stripper column 11, the column top temperature is usually 85 to 120° C., and the column bottom temperature is usually 100 to 130° C.

As illustrated in FIG. 2, the absorption liquid as a remaining part after ethylene oxide is stripped is extracted as the column bottom liquid of the stripper column 11, supplied to an upper part of the absorption column 2 as the absorption liquid of the absorption column 2, and can be circulated and used. In order to adjust the composition of the absorption liquid, fresh water or the above-described additive as necessary may be supplied to the absorption column 2 through a conduit disposed separately. The concentration of ethylene glycol in the absorption liquid supplied to the absorption column 2 is preferably maintained constant. Therefore, apart of the absorption liquid circulating between the absorption column 2 and the stripper column 11 is extracted from the column bottom part of the stripper column 11. Here, the column bottom liquid of the stripper column 11 does not contain ethylene oxide substantially. Specifically, the concentration of ethylene oxide contained in the column bottom liquid is preferably 10 ppm by weight or less, more preferably 0.5 ppm by weight or less. The column bottom liquid contains ethylene glycol produced in the absorption liquid as a by-product between the ethylene oxidation reaction step and the ethylene oxide stripping step. A part thereof is extracted through a conduit 21 and 22. The extracted liquid is subjected to a combustion treatment or an ethylene glycol concentration step for concentrating and recovering ethylene glycol contained therein. Furthermore, in some cases, it is possible to recover ethylene glycol contained in the extracted liquid as a fiber grade product by performing a chemical treatment and, in some cases, a physical treatment to the ethylene glycol as it is or the ethylene glycol after being subjected to the ethylene glycol concentration step. The chemical treatment is, for example, disclosed in JP 45-9926 B or JP 04-28247 B. In the meantime, the column bottom liquid of the stripper column 11 also contains a low boiling point impurity such as formaldehyde and a high boiling point impurity such as acetaldehyde or acetic acid. Therefore, as described above, accumulation of these impurities in the absorption liquid circulated into the absorption column 2 can be advantageously prevented by extracting a part thereof to the outside of the system. On the other hand, the column bottom liquid of the stripper column, not extracted through the conduit 22, passes through a heat exchanger 13. The column bottom liquid of the stripper column is thereby cooled by heat exchange with the column bottom liquid of the absorption column 2 to be circulated into the column top part of the absorption column 2.

The ethylene oxide-containing stripped substance stripped from the column top part of the stripper column 11 is fed through the conduit 20 to a stripper column condenser 25 in which cooling water passes through conduits 23 and 24. The condensed liquid is refluxed to the column top part of the stripper column 11 through a conduit 26. Uncondensed steam is supplied to a dehydrating column 28 (FIG. 3) through a conduit 27.

The ethylene oxide-containing steam supplied to the dehydrating column 28 comes into contact with a liquid to be refluxed through a conduit 29, and becomes steam having a higher concentration of ethylene oxide. A liquid extracted from the column bottom and having a low concentration of ethylene oxide is fed to the stripper column condenser 25 through a conduit.

The ethylene oxide-containing steam discharged from the column top part of the dehydrating column 28 is fed through a conduit 30 to a dehydrating column condenser 33 in which cooling water passes through conduits 31 and 32. A part of the condensed liquid is refluxed to the column top part of the dehydrating column 28 through the conduit 29. Uncondensed steam (ethylene oxide-containing uncondensed gas) of the dehydrating column condenser 33 is supplied to an ethylene oxide reabsorption column (not illustrated) through a conduit 34. In the ethylene oxide reabsorption column, as in the above-described absorption column 2, ethylene oxide is reabsorbed by counter flow contact with the absorption liquid. Here, the composition and the pH of the absorption liquid used for reabsorption of ethylene oxide in the reabsorption column 35, forms of the reabsorption column (plate column type or packed column type), operation conditions, and the like are similar to those described above for the absorption column 2. The column bottom liquid of the ethylene oxide reabsorption column is circulated into the purification system (in the present embodiment, specifically the stripper column 11) similarly to the above-described column bottom liquid of the absorption column 2. On the other hand, the uncondensed gas not absorbed in the ethylene oxide reabsorption column is discharged from the column top part. The uncondensed gas discharged from the ethylene oxide reabsorption column is boosted by a pressurizing means, and then can be circulated into the absorption column 2. However, the uncondensed gas is more preferably supplied to the carbon dioxide gas absorption column 7. The uncondensed gas contains a large amount of carbon dioxide gas (usually about 5 to 60% by volume). Therefore, by such a structure, a concentration of the carbon dioxide gas in the gas supplied from the absorption column 2 to the carbon dioxide gas absorption column 7 can be increased. As a result, occurrence of problems caused by the increase in the amount of the carbon dioxide gas in the gas supplied to the carbon dioxide gas absorption column 7 is prevented. It is possible to efficiently recover the carbon dioxide gas from the process for producing ethylene oxide. More specifically, at least one of the following industrially extremely advantageous effects is obtained. That is, reduction in the amount of steam input into the reboiler 9 of the carbon dioxide gas stripper column 8, reduction in the input amount of the carbon dioxide gas absorption promoter, reduction in the boosting blower power due to reduction in the flow rate of the gas fed from the absorption column 2 to the carbon dioxide gas absorption column 7, reduction in size of the equipment of the carbon dioxide gas absorption column 7, and improvement of the yield of ethylene oxide due to reduction in the concentration of the carbon dioxide gas at the entrance of the ethylene oxidation reactor 1.

The remaining part of the condensed liquid of the dehydrating column condenser 33 is supplied to a light fraction separation column 37 through a conduit 36. Ethylene oxide steam containing a light fraction is heated using a reboiler 38 of the light fraction separation column 37 with a heating medium such as water vapor through a conduit 39, and is fed through a conduit 40 from the column top part of the light fraction separation column 37 to a light fraction separation column condenser 43 in which cooling water passes through conduits 41 and 42. The condensed liquid is refluxed to the column top part of the light fraction separation column 37 through a conduit 44. The uncondensed steam (ethylene oxide-containing uncondensed gas) of the light fraction separation column condenser 43 is supplied through a conduit 45 to the above-mentioned ethylene oxide reabsorption column to recover ethylene oxide.

The column bottom liquid of the light fraction separation column 37 is supplied to an ethylene oxide purification column (hereinafter, also simply referred to as "purification column") 47 through a conduit 46. The purification column 47 is provided with a reboiler 48 in a column bottom part thereof. In the present embodiment, water vapor having a pressure of about 0.05 to 0.10 MPa gauge is supplied to the reboiler 48 of the purification column 47 as a heating medium for heating the reboiler 48. However, the heating medium may be another substance. For example, a glycol aqueous solution, warm water, or the like is used.

The present invention is characterized in that the heating medium for heating the reboiler 48 of the purification column 47 is heated by heat exchange with the above-described exhaust gas from the column top part of the carbon dioxide gas stripper column 8. In order to achieve this, a heat exchanger 57 is disposed on a circulation path 56 to the reboiler 48 of the above-described heating medium (water vapor). The exhaust gas from the column top part of the carbon dioxide gas stripper column 8 is supplied to the heat exchanger 57 through a conduit 58. This causes heat exchange with the above-described heating medium (water vapor) to heat the heating medium (water vapor). As illustrated in FIG. 1, the exhaust gas after being subjected to the heat exchange in the heat exchanger 57 may be circulated into the gas-liquid separation part 10 of the carbon dioxide gas stripper column 8 again, and then may be purged into the atmosphere.

Here, it is not preferable to operate the purification column 47 at a high temperature because of safety. Therefore, the operation temperature of the purification column 47 is characterized by being lower than that of another distillation column. The present inventors have studied and found that the column top temperature of the carbon dioxide gas stripper column 8 is a relatively low temperature of 87° C., and that an exhaust gas at this temperature can be used as a heat source of the purification column 47. That is, the exhaust gas from the column top part of the carbon dioxide gas stripper column 8 is steam containing a carbon dioxide gas. In order to increase a heat recovery efficiency of the steam in the exhaust gas, a difference in temperature between substances subjected to heat exchange is preferably larger. Therefore, the above-described temperature when the above-described exhaust gas is used for heat exchange is preferably lower.

As described above, by supply of the heating medium to the reboiler 48, purification is performed at a column bottom temperature of the purification column 47 of 35 to 80° C. at a column bottom pressure of the purification column 47 of 0.10 to 0.80 MPa gauge. Ethylene oxide steam at a column top temperature of 12 to 75° C. at a column top part pressure of 0.10 to 0.80 MPa gauge is fed from the column top part of the purification column 47 to the purification column condenser 51 in which cooling water passes through conduits 49 and 50. Ethylene oxide is liquefied in the purification column condenser 51. Apart thereof is supplied to the column top part of the purification column 47 through a conduit 52 as a reflux liquid, and the remaining part thereof is extracted through a conduit 53 as a product ethylene oxide (product EO). The uncondensed steam (ethylene oxide-containing uncondensed gas) of the purification column condenser 51 is supplied through a conduit 54 to the ethylene oxide reabsorption column to recover ethylene oxide.

The column bottom liquid of the purification column 47 is extracted through a conduit 55 if necessary to separate a heavy fraction of a high boiling point impurity such as acetaldehyde, water, acetic acid and so on.

As described above, the uncondensed steam discharged from the purification system (in the embodiment illustrated in FIG. 3, uncondensed steam derived from the dehydrating column condenser 33, the light fraction separation column condenser 43, and the purification column condenser 51) contains ethylene oxide. Therefore, the uncondensed steam is supplied to the above-described ethylene oxide reabsorption column.

EXAMPLES

Hereinafter, the embodiment of the present invention will be described in more detail using Examples. However, the technical range of the present invention is not limited only to the following embodiment.

Comparative Example

Figure 3:
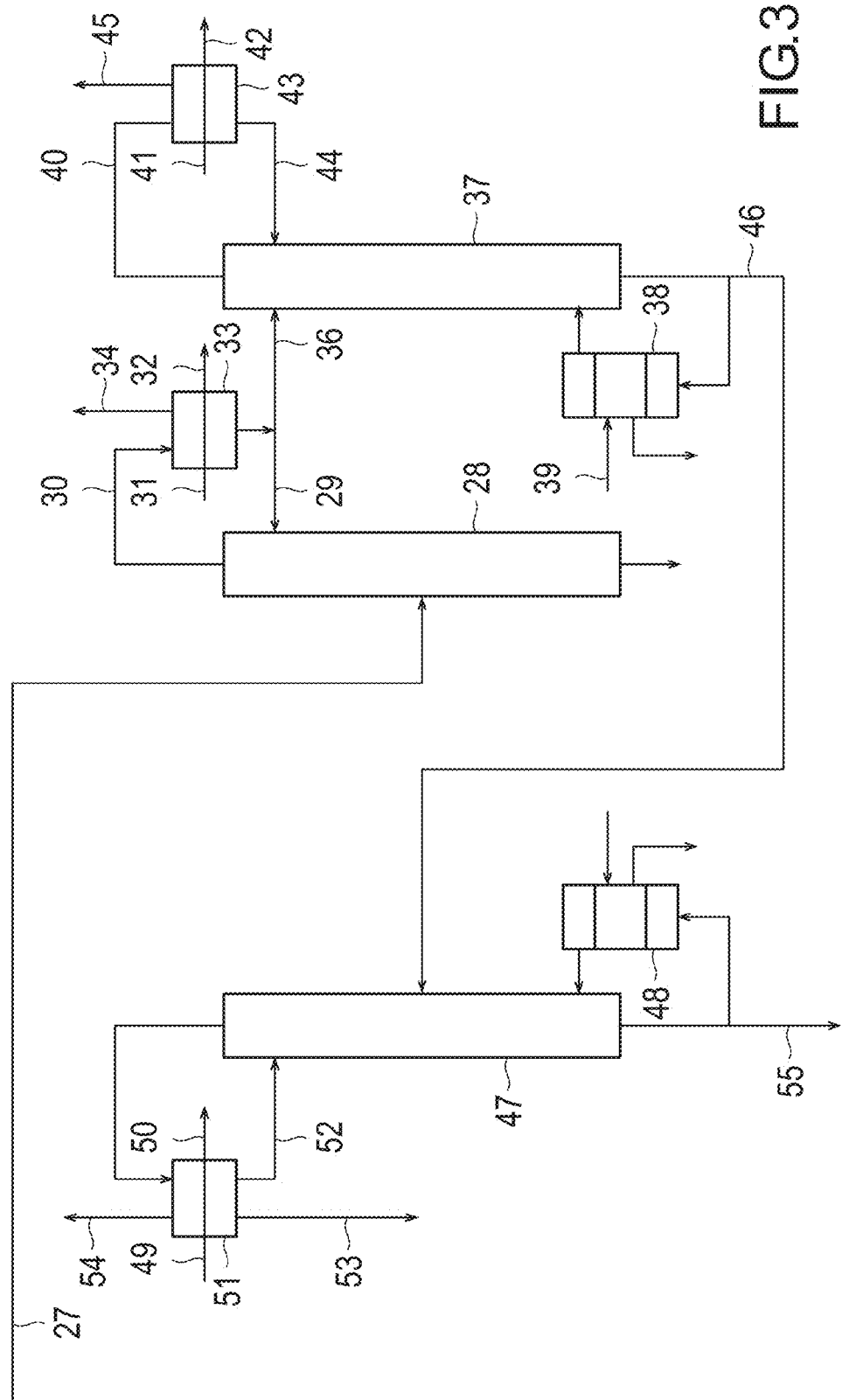
FIG. 3 is a block diagram illustrating a structure example of a purification step until the stripped ethylene oxide is finally purified.
Figure 4:
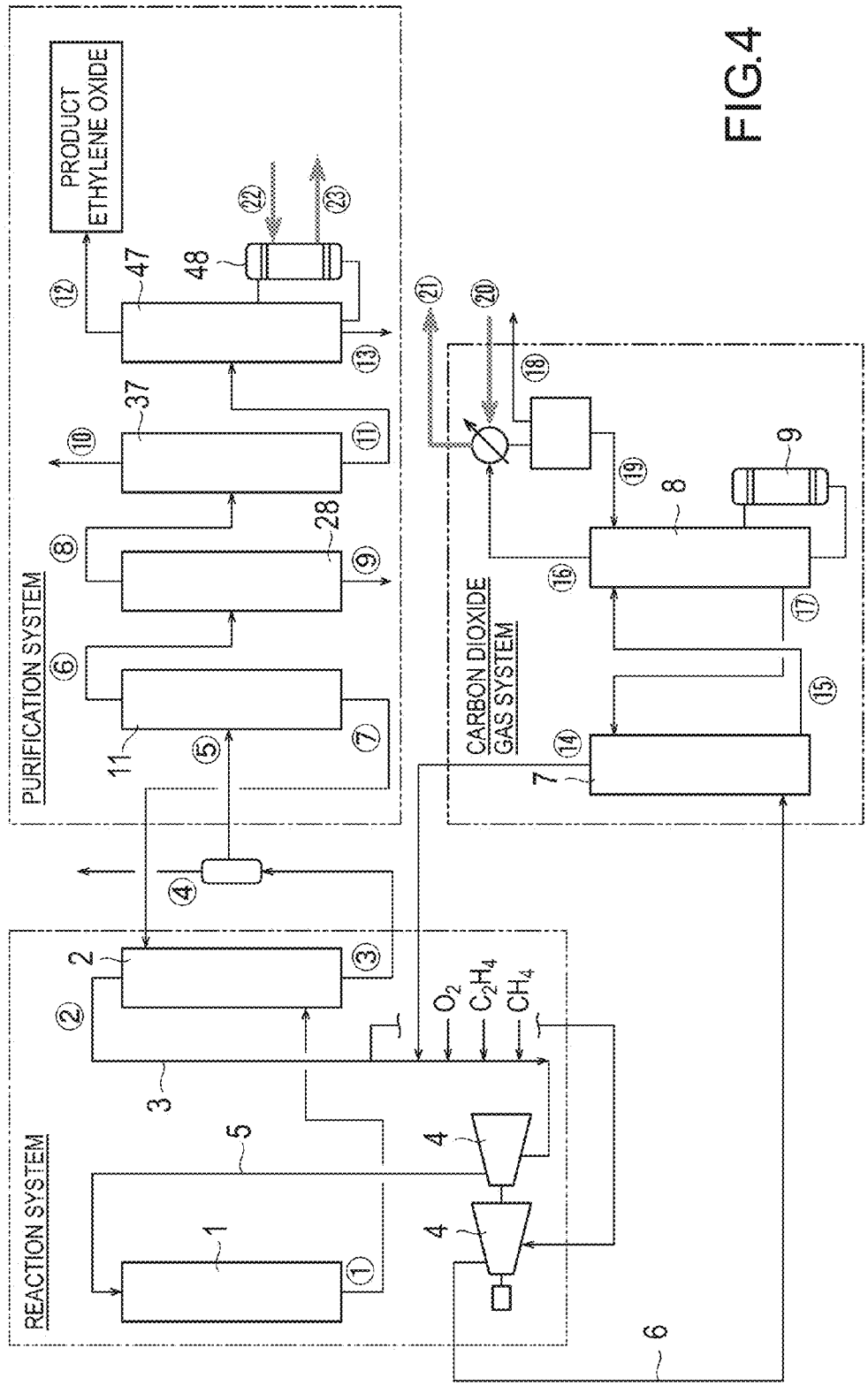
FIG. 4 is a block diagram illustrating a structure example of a production process for performing a method for producing ethylene oxide in the related art.

Ethylene oxide was produced by a process for producing ethylene oxide illustrated in FIGS. 2 to 4. Here, the following Table 1 shows component amounts, operation conditions, and amounts of water vapor and cooling water required for the operation, in each portion of the circled numbers 1 to 23 illustrated in FIG. 4, during stationary operation of the present Comparative Example.

TABLE 1

|  | ① | ② | ③ | ④ | ⑤ | ⑥ | ⑦ | ⑪ | ⑫ |
|---|---|---|---|---|---|---|---|---|---|
| Inert gas % by weight | 84 | 87 | 0.06 | 24.22 |  |  |  |  |  |
| Carbon dioxide gas % by weight | 12.6 | 13 | 0.11 | 30.1 | 0.04 | 0.67 |  |  |  |

TABLE 1-continued

| | | | | | | | | |
|---|---|---|---|---|---|---|---|---|
| Ethylene oxide % by weight | 2.5 | | 2.73 | 30.34 | 2.6 | 52.95 | | 99.97 | 100 |
| Water % by weight | 0.9 | | 88.46 | 15.34 | 88.62 | 46.34 | 91 | 0.01 | |
| Ethylene glycol % by weight | | | 8.64 | | 8.74 | 0.04 | 9 | | |
| Others % by weight | | | | | | | | 0.02 | |
| Flow rate kg/h | 336825 | 324325 | 308100 | 810 | 307290 | 15500 | 295600 | 7600 | 7594 |
| Pressure MPa | 23 | 22.5 | 3.4 | 3.4 | 3.4 | 0.4 | 5 | 2.4 | 1.8 |
| Temperature °C | 70 | | 105.5 | 104.7 | 104.7 | 99.6 | 51.5 | 45 | |
| Water vapor kg/h | | | | | | | | | |
| Cooling water kg/h | | | | | | | | | |

| | ⑬ | ⑮ | ⑰ | ⑱ | ⑲ | ⑳ | ㉒ |
|---|---|---|---|---|---|---|---|
| Inert gas % by weight | | 0.1 | | 1.0 | | | |
| Carbon dioxide gas % by weight | | 2.9 | | 97.2 | | | |
| Ethylene oxide % by weight | | | | | | | |
| Water % by weight | | 67.2 | 69.7 | 1.8 | 100 | | |
| Ethylene glycol % by weight | | 0.2 | 0.2 | | | | |
| Others % by weight | | 29.6 | 30.0 | | | | |
| Flow rate kg/h | 6 | 209353 | 203372 | 5981 | 5430 | | |
| Pressure MPa | 1.8 | 0.13 | 22.9 | | | | 2.2 |
| Temperature °C | 51 | 100.7 | 103 | 31 | 31 | | 135 |
| Water vapor kg/h | | | | | | | 8000 |
| Cooling water kg/h | | | | | | 82 | |

Example

Ethylene oxide was produced by a process for producing ethylene oxide illustrated in FIGS. 1 to 3. Here, the following Table 2 shows component amounts, operation conditions, and amounts of water vapor and cooling water required for the operation, in each portion of the circled numbers 1 to 22 illustrated in FIG. 1, during stationary operation of the present Example.

TABLE 2

| | ① | ② | ③ | ④ | ⑤ | ⑥ | ⑦ | ⑪ | ⑫ | ⑬ | ⑮ |
|---|---|---|---|---|---|---|---|---|---|---|---|
| Inert gas % by weight | 84 | 87 | 0.06 | 24.22 | | | | | | | 0.1 |
| Carbon dioxide gas % by weight | 12.6 | 13 | 0.11 | 30.1 | 0.04 | 0.67 | | | | | 2.9 |
| Ethylene oxide % by weight | 2.5 | | 2.73 | 30.34 | 2.6 | 52.95 | | 99.97 | 100 | | |
| Water % by weight | 0.9 | | 88.46 | 15.34 | 88.62 | 46.34 | 91 | 0.01 | | | 67.2 |
| Ethylene glycol % by weight | | | 8.64 | | 8.74 | 0.04 | 9 | | | | 0.2 |
| Others % by weight | | | | | | | | 0.02 | | | 29.6 |

TABLE 2-continued

| | | | | | | | | | | |
|---|---|---|---|---|---|---|---|---|---|---|
| Flow rate kg/h | 336825 | 324325 | 308100 | 810 | 307290 | 15500 | 295600 | 7600 | 7594 | 6 | 209353 |
| Pressure Kg/cm²G | 23 | 22.5 | 3.4 | 3.4 | 3.4 | 0.4 | 5 | 2.4 | 1.8 | 1.8 | 0.13 |
| Temperature °C | 70 | | 105.5 | 104.7 | 104.7 | 99.6 | 51.5 | 45 | | 51 | 100.7 |
| Water vapor kg/h | | | | | | | | | | | |
| Cooling water kg/h | | | | | | | | | | | |

| | ⑯ | ⑰ | ⑱ | ⑲ | ⑳ | ㉑ | ㉒ | ㉓ | ㉓ |
|---|---|---|---|---|---|---|---|---|---|
| Inert gas % by weight | 0.53 | | 0.53 | 1.01 | | | | | |
| Carbon dioxide gas % by weight | 50.93 | | 50.93 | 97.18 | | | | | |
| Ethylene oxide % by weight | | | | | | | | | |
| Water % by weight | 68.19 | 69.7 | 68.19 | 1.81 | 100 | 100 | 100 | 100 | 100 |
| Ethylene glycol % by weight | | 0.2 | | | | | | | |
| Others % by weight | | 30.0 | | | | | | | |
| Flow rate kg/h | 11411 | 203372 | 11411 | 5981 | 5430 | 120000 | 5500 | | 120000 |
| Pressure Kg/cm²G | | 22.9 | | | | | 2.2 | | |
| Temperature °C | 70 | 103 | 70 | 31 | 31 | 67 | 135 | | 80 |
| Water vapor kg/h | | | | | | | | | |
| Cooling water kg/h | | | | | | | | | |

The results shown in Tables 1 and 2 indicate that the recovered heat amount is 530 Mcal/hr. Further, if it is assumed that the production amount per year of ethylene oxide is 67,000 tons, and C heavy oil is used as a fuel of a boiler for generating water vapor used as a heat source for process operation, 9000 tons of water vapor input into the reboiler 9 of the carbon dioxide gas stripper column 8 is reduced per year. In addition, similarly, 1500 tons of carbon dioxide ($CO_2$) generated by combustion of C heavy oil is also reduced per year.

REFERENCE SIGNS LIST

1: ethylene oxidation reactor
2: ethylene oxide absorption column
4: boosting blower
7: carbon dioxide gas absorption column
8: carbon dioxide gas stripper column
9: reboiler
10: gas-liquid contact part
11: ethylene oxide stripper column
13: heat exchanger
14: reboiler
16: gas-liquid separation tank
19: stripper column reboiler
25: stripper column condenser
28: dehydrating column
33: dehydrating column condenser
37: light fraction separation column
38: light fraction separation column reboiler
43: light fraction separation column condenser
47: ethylene oxide purification column
48: purification column reboiler
51: purification column condenser
56: circulation path
57: heat exchanger
58: conduit

The invention claimed is:

1. A method for producing ethylene oxide comprising:
an ethylene oxidation reaction step in which ethylene is subjected to catalytic vapor-phase oxidation using a molecular oxygen-containing gas in the presence of a silver catalyst;
supplying an ethylene oxide-containing reaction product gas produced in the ethylene oxidation reaction step to an ethylene oxide absorption column;
bringing the reaction product gas into contact with an absorption liquid supplied to the ethylene oxide absorption column;
supplying an ethylene oxide-containing column bottom liquid of the ethylene oxide absorption column to an ethylene oxide purification system;
purifying ethylene oxide in the ethylene oxide purification system;
supplying at least a part of a carbon dioxide gas-containing gas discharged from a column top part of the ethylene oxide absorption column to a carbon dioxide gas absorption column;
extracting a carbon dioxide gas-rich absorption liquid obtained by contact of the carbon dioxide gas-containing gas with an absorption liquid as a column bottom liquid of the carbon dioxide gas absorption column;

supplying the carbon dioxide gas-rich absorption liquid to an upper part of the carbon dioxide gas stripper column;

stripping the carbon dioxide gas from the carbon dioxide gas-rich absorption liquid; and discharging the carbon dioxide gas from a column top part of the carbon dioxide gas stripper column as an exhaust gas, wherein the ethylene oxide purification system includes an ethylene oxide purification column provided with a reboiler in a lower part thereof, and a heating medium for heating the reboiler is heated by heat exchange with the exhaust gas.

* * * * *